(12) United States Patent
Italiaie

(10) Patent No.: US 11,712,274 B2
(45) Date of Patent: Aug. 1, 2023

(54) SYSTEMS AND METHODS OF USING A DRIVER INSTRUMENT

(71) Applicant: Warsaw Orthopedic, Inc., Warsaw, IN (US)

(72) Inventor: Christel Italiaie, Memphis, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 66 days.

(21) Appl. No.: 17/323,269

(22) Filed: May 18, 2021

(65) Prior Publication Data
US 2022/0370101 A1    Nov. 24, 2022

(51) Int. Cl.
   *A61B 17/70* (2006.01)
   *A61B 17/88* (2006.01)
   *A61B 17/00* (2006.01)

(52) U.S. Cl.
   CPC ...... *A61B 17/7082* (2013.01); *A61B 2017/00367* (2013.01)

(58) Field of Classification Search
   CPC ............ A61B 17/7082; A61B 17/7076; A61B 17/7078; A61B 17/7079; A61B 17/708; A61B 17/7083; A61B 17/8875; A61B 17/8886; A61B 17/888; B25B 15/02; B25B 15/04; B25G 1/04; B25G 1/0043; B25G 1/06
   USPC ................................... 606/99, 104.86 A, 279
   See application file for complete search history.

(56) References Cited

U.S. PATENT DOCUMENTS

| 9,078,709 | B2 | 7/2015 | McBride |
| 10,245,087 | B2 | 4/2019 | Donner et al. |
| 10,779,893 | B2 | 9/2020 | Elliott et al. |
| 2009/0030420 | A1* | 1/2009 | Runco ............... A61B 17/7086 606/99 |
| 2011/0313477 | A1* | 12/2011 | McLean ............ A61B 17/7002 606/86 A |

(Continued)

FOREIGN PATENT DOCUMENTS

WO    WO-2021046235 A1 *    3/2021    ......... A61B 17/1671

OTHER PUBLICATIONS

Radius® Spinal System Surgical Technique, Stryker Spine, TLRAD-ST-1_Rev-1, www.stryker.com, © 2014 Stryker.

(Continued)

*Primary Examiner* — Eduardo C Robert
*Assistant Examiner* — David C Comstock
(74) *Attorney, Agent, or Firm* — Fox Rothschild LLP

(57) ABSTRACT

Systems and method of using a surgical driver instrument are provided. The driver instrument includes a driver shank having a proximal end including a head connector for a bone construct. The instrument includes an inner sleeve having a length and configured to receive the driver shank therein and a handle member having a first end and a second end. The inner sleeve and the driver shank have a non-threaded connection. The instrument includes an outer sleeve connected to the second end and concentric with the inner sleeve and a sleeve actuator assembly coupled to the handle member. The sleeve actuator assembly includes a first position where a portion of the length of the inner sleeve extends out from the handle member and a second position where the portion of the length of the inner sleeve that is extended from the handle member is retracted into the handle member.

10 Claims, 12 Drawing Sheets

(56) References Cited

U.S. PATENT DOCUMENTS

| | | | |
|---|---|---|---|
| 2014/0114363 A1* | 4/2014 | Stevenson | A61B 17/7082 606/305 |
| 2019/0254729 A1 | 8/2019 | Rohlfing et al. | |
| 2021/0059724 A1* | 3/2021 | Rezach | A61B 17/7082 |

OTHER PUBLICATIONS

CD Horizon® Solera® 5.5/6.0 Spinal System, Surgical Technique, www.myspinetools.com, © 2014 Medtronic, Inc., UC201405514EE PMD01 2892-1.0.

* cited by examiner

SYSTEMS AND METHODS OF USING A DRIVER INSTRUMENT

FIELD

The present technology is generally related to medical devices for the treatment of musculoskeletal disorders, and more particularly to a systems and methods of using a driver instrument.

BACKGROUND

Spinal disorders of the spine may result in symptoms, such as without limitation, nerve damage, and partial or complete loss of mobility and chronic pain. Surgical treatment of these spinal disorders includes correction, fusion, fixation, discectomy, laminectomy and implantable prosthetics, for example. As part of these surgical treatments, vertebral rods and bone fasteners are often used to provide stability to a treated region. During surgical treatment, a surgeon uses various surgical instruments, such as drivers, to implant bone fasteners to a surgical site.

The drivers may have a threaded connection between a support sleeve and driver shank, for example. However, the driver may become inadvertently unthreaded such that the shank can toggle. This may affect the mated connection between the driver shank and the bone fastener.

This disclosure describes an improvement over these prior art technologies.

SUMMARY

The techniques of this disclosure generally relate to systems and methods for using a driver instrument. The system includes, for example, a driver shank and a shank adaptor with inner sleeve having a non-threaded connection, for example, to the driver shank.

In one aspect, the present disclosure provides a driver instrument that may include a driver shank having a proximal end including a head connector for a bone construct and an inner sleeve having a length and configured to receive the driver shank therein. The inner sleeve and the driver shank can have a non-threaded connection. The driver instrument includes, for example, a handle member having a first end and a second end and an outer sleeve connected to the second end and concentric with the inner sleeve. The driver instrument can include a sleeve actuator assembly coupled to the handle member. The sleeve actuator assembly having, for example, a first position where a portion of the length of the inner sleeve extends out from the handle member and a second position where the portion of the length of the inner sleeve that is extended from the handle member is retracted into the handle member.

In another aspect, the disclosure provides a system that can include a bone construct having a head and a surgical driver instrument. The surgical driver instrument can include a driver shank having a proximal end including a head connector for axial rotation of the bone construct. The instrument includes, for example, an inner sleeve having a length and configured to receive the driver shank therein. The inner sleeve and the driver shank can have a non-threaded connection. The instrument can include a handle member having a first end and a second end and an outer sleeve connected to the second end and concentric with the inner sleeve. The instrument may further include a sleeve actuator assembly coupled to the handle member. The sleeve actuator assembly may have a first position where a portion of the length of the inner sleeve extends out from the handle member and a second position where the portion of the length of the inner sleeve that is extended from the handle member is retracted into the handle member.

In another aspect, a method is provided that includes providing a driver instrument and engaging a driver shank with a bone construct when an inner sleeve is extended. The method includes rotating the bone construct with the driver shank when the inner sleeve is retracted.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1A:
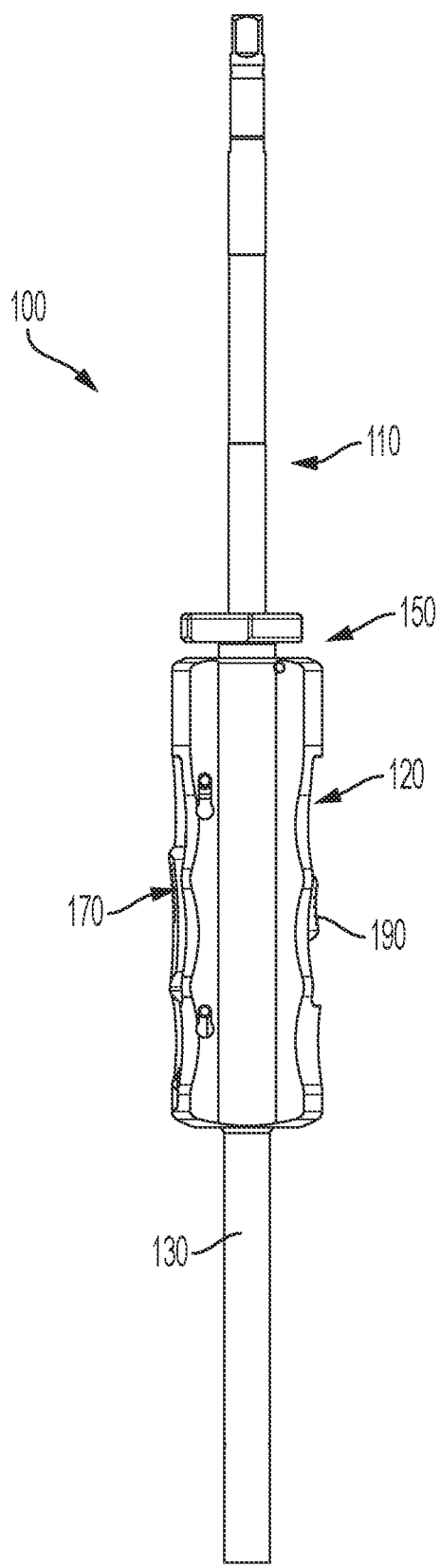
FIG. 1A is a side view that illustrates components of a surgical instrument system having a first driver instrument.

The embodiments of the surgical instrument system are discussed, by means of example, in terms of medical devices for the treatment of musculoskeletal disorders and more particularly, in terms of a surgical system and a method for treating a spine, but may be useful for other purposes. In the embodiments, the system may include a surgical driver instrument that may include a driver shank, a shank adaptor with inner sleeve having a non-threaded connection, for example, to the driver shank, and the related methods of use that can be employed with spinal bone constructs including bone fasteners and connectors that provide a surgical implant system for spine surgeons.

The embodiments of the surgical instrument system may be used for posterior, cervical or non-cervical fixation as an adjunct to fusion for the following indications: degenerative disc disease (defined as back pain of discogenic origin with degeneration of the disc confirmed by history and radiographic studies), spondylolisthesis, trauma (i.e., fracture or dislocation), spinal stenosis, curvatures (i.e., scoliosis, kyphosis, or lordosis), tumor, pseudarthrosis, and/or failed previous fusion.

The system of the present disclosure may be understood more readily by reference to the following detailed description of the embodiments taken in connection with the accompanying drawing figures that form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, front, back, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of and/or reducing the likelihood of a certain disease or undesirable condition (e.g., preventing or reducing the likelihood of the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

Figure 1B:
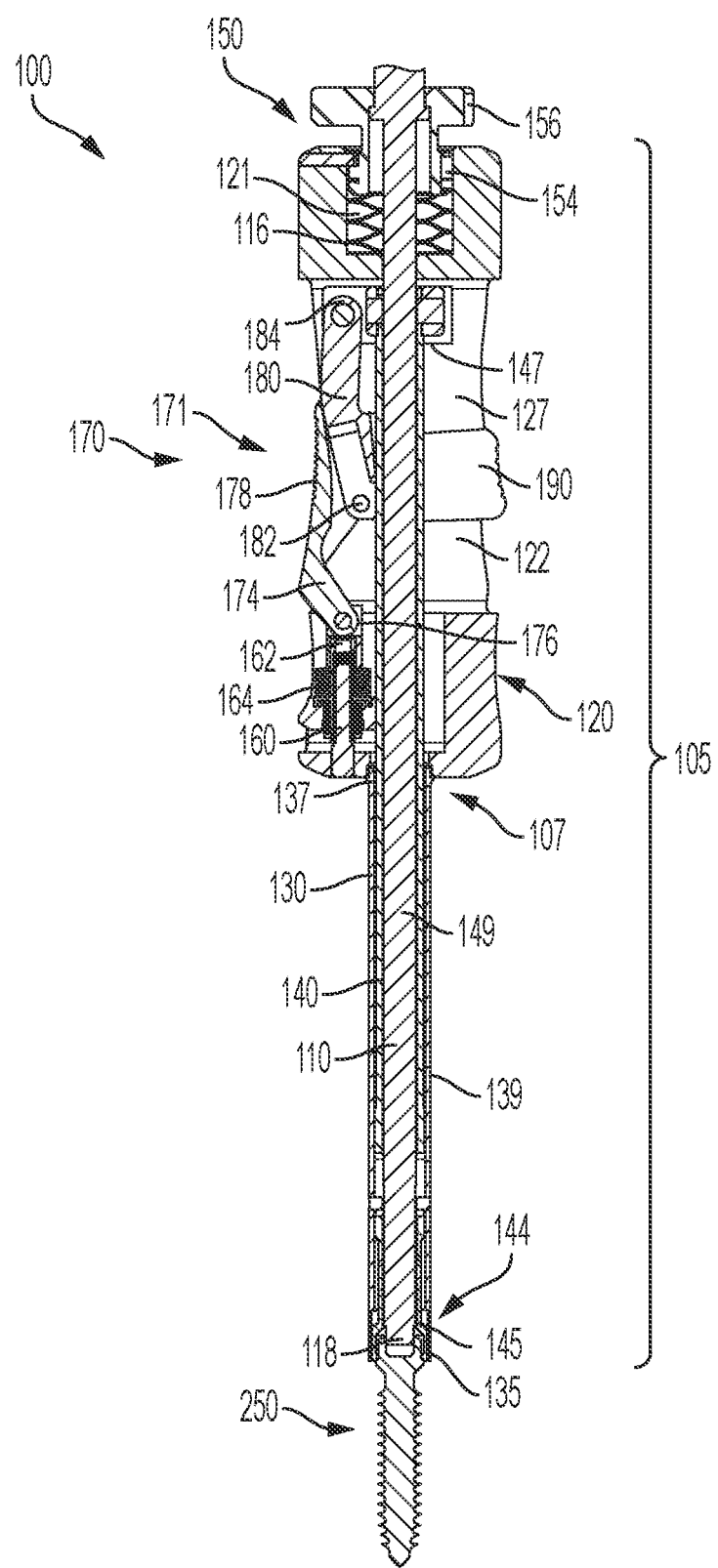
FIG. 1B is a cross-sectional view that illustrates components of a surgical instrument system having the first driver instrument.

The following discussion includes a description of a surgical instrument system including a driver instrument, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1A-1B, components of a surgical instrument system 100 are illustrated, in accordance with the principles of the disclosure.

The components of system 100 can be fabricated from biologically acceptable materials suitable for medical applications, including metals, synthetic polymers, ceramics and bone material and/or their composites. For example, the components of system 100, individually or collectively, can be fabricated from materials such as stainless steel alloys, aluminum, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologic Inc.), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, and their combinations.

Various components of system 100 may have material composites, including the above materials, to achieve various desired characteristics such as strength, rigidity, elasticity, compliance, biomechanical performance, durability and radiolucency or imaging preference. The components of system 100, individually or collectively, may also be fabricated from a heterogeneous material such as a combination of two or more of the above-described materials. The one or more components of system 100 may be monolithically formed, integrally connected or include fastening elements and/or instruments, as described herein.

The system 100 may include surgical driver instrument 105 and be employed, for example, with an open or mini-open, minimal access and/or minimally invasive including percutaneous surgical technique to deliver and fasten an implant at a surgical site within a body of a patient, for example, a section of a spine. In one embodiment, the components of system 100 may be configured to implant and/or fix a bone fastener, such as a pedicle screw, or other implants within tissue for a surgical treatment to treat various spine pathologies, such as those described herein.

FIGS. 1A-1B a side view and a cross-sectional view that illustrate components of a surgical instrument system 100 having a first driver instrument 105. The system 100 of FIGS. 1A-1B will also be described in relation to FIG. 2, a side view that illustrates an example bone fastener 250 of the surgical instrument system 100. The first driver instrument 105 may be a CAM driver instrument or an over-center CAM driver instrument. The system 100 may also include a bone construct 250 which may be an anchor or bone fastener. The bone construct 250 will sometimes be referred to herein below as a "bone fastener 250." The bone fastener 250 may be configured to mate with the design of the driver instrument 105. The driver instrument 105 may include a shank adapter 107 configured to support a driver shank 110 via a non-threaded connection. The driver shank 110 may drive a bone fastener shank 255 of bone fastener 250 without a tulip head attached thereto. The driver shank 110 may include a driver bit 118 configured to mate with a socket in the head of the bone fastener 250, the driver bit 118 being positioned at the proximal end of the driver shank 110. The driver instrument 105 may allow rotation or derotation to be applied directly to the driver shank 110. The driver instrument 105 may have the ability to rotate the driver shank mated to a socket of a bone construct.

The first driver instrument 105 may include a handle member 120 and an outer sleeve 130 coupled to a first (bottom) end of the handle member 120. The outer sleeve 130 includes a proximal end 135, a distal end 137, and an outer sleeve body 139 that extends from the proximal end 135 to the distal end 137. The distal end 137 may be affixed to the first end of the handle member 120.

The driver instrument 105 may include an inner sleeve 140 having a proximal end 144, a distal end 147, and an inner sleeve body 149 that extends from the proximal end 144 to the distal end 147. The proximal end 144 may include a collet member 145. An exemplary interface between the outer sleeve 130 and the inner sleeve 140 is described in more detail in relation to FIG. 3.

Figure 4A:
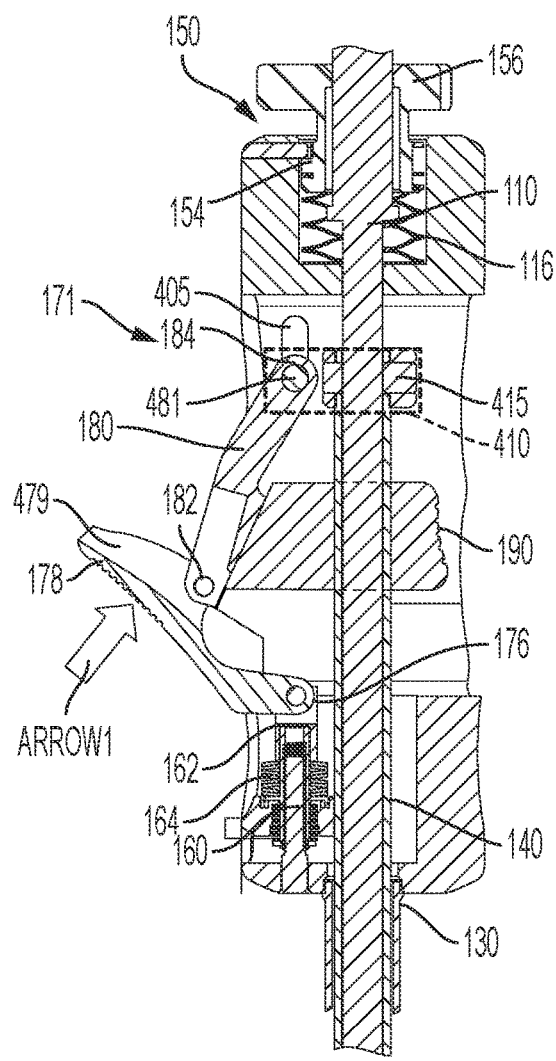
FIG. 4A illustrates a cross-sectional view of the locking element in an unlocked position, the inner sleeve in a retracted position and the release button in a recessed position.
Figure 4B:
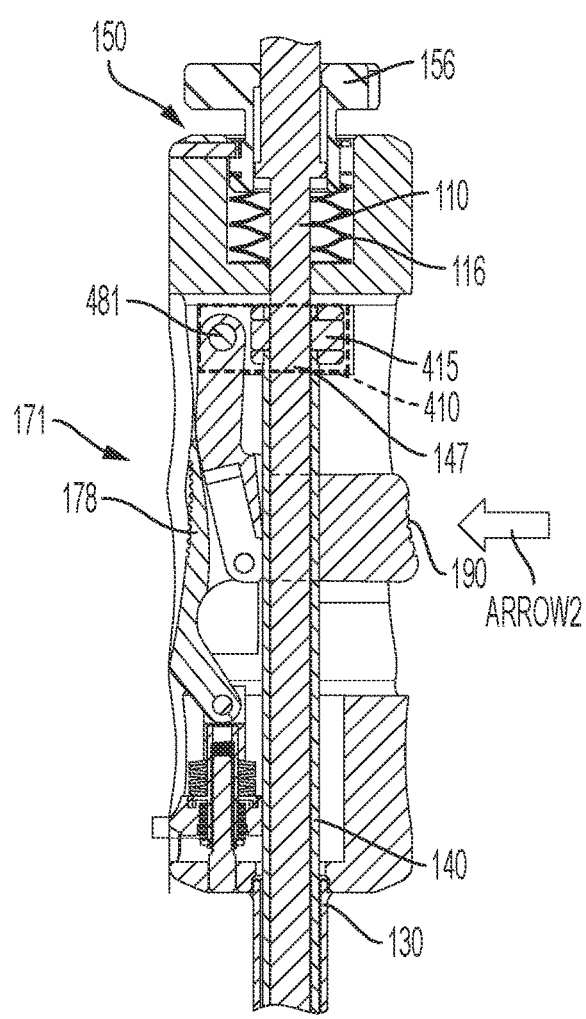
FIG. 4B illustrates a cross-sectional view of the locking element in a locked position, the inner sleeve in an extended position and the release button in an extended position.

The handle member 120 may be configured to unlock the inner sleeve to extend the inner sleeve 140 from the first (bottom) end of the handle member 120 and lock the inner sleeve 140 to a retracted position within the handle member 120, as shown in FIG. 1B and FIG. 4B. The handle member 120 may include a handle member body 122 with a first cavity 121 and a second cavity 127. The first cavity 121 may be configured to mount therein a portion of the driver shank 110. The driver shank 110 may include a driver mount 150 having a flange 154. The driver shank 110 may be mounted to the handle member body 122 via the driver mount 150. Specifically, the driver shank 110 is coupled to the second (top) end of the handle member 120, the second end and the first end are opposite ends.

The shank adapter 107 may include a spring 116 housed in the first cavity 121 below the flange 154. The spring 116 may be helically wound around die driver shank 110. In various embodiments, the driver mount 150 may include a collar 156. In operation, the collar 156 may limit the distance of travel by the driver shank 110 in a direction toward the hone fastener 250 or the first (bottom) end of the handle member 120.

In some embodiments, the surgical instrument system 100 may be configured to provide a spring-biased coaxial connection between the driver shank 110 and the bone fastener 250 via spring 116. In some embodiments, the surgical instrument system 100 may include a non-threaded connection between the driver instrument 105 and the bone fastener 250 to form a co-axial connection.

Figure 2:
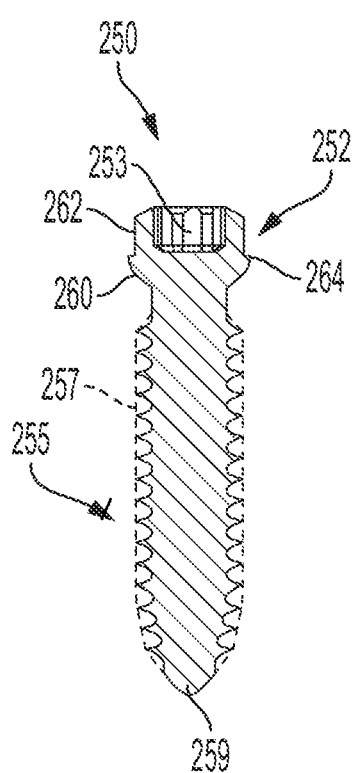
FIG. 2 is a side view that illustrates an example bone fastener of the surgical instrument system.

Referring also to FIG. 2, the bone fastener 250 may include a head 252 (e.g., polyaxial head, uni-axial head, monoaxial head, etc.) at a proximal end relative to the driver bit 118. The bone fastener 250 may include a bone fastener shank 255 having, for example, a threaded portion 257 and a tip 259 at a distal end. The head 252 may include a driver socket 253 configured to receive and mate with the driver bit 118. The interface between the driver socket 253 and the driver bit 118 may limit rotational movement of the driver bit 118 within the driver socket 253.

The head 252 may include a first head portion 260 having a first circumference and a second head portion 262 having second circumference. The second circumference may be reduced relative to the first circumference by a step reduction circumferentially in an outer surface of the head 252. The fastener shank 255 may be coupled to the first head portion 260. The first head portion 260 may provide a shoulder 264 to seat the collet member 145 of the inner sleeve 140. The second head portion 262 may have the socket 253 formed therein. The shoulder 264 may be a demarcation between the first head portion 260 and the second head portion 262. The collet member 145 may be slipped on the second head portion 262, as will be described in more detail in relation to FIGS. 5B-5C.

Returning again to FIG. 1B, the driver instrument 105 may include a sleeve actuator assembly 170 housed in the second cavity 127 and engaged with the inner sleeve 140 to selectively retract a portion of the length of the inner sleeve 140 and driver shank 110 into the handle member 120 or, alternately extend a portion of the length of the inner sleeve 140 and driver shank 110 away from the first (bottom) end of the handle member 120. The assembly 170 may include a locking element 171 with components accessible externally relative to the cavity 127 of the handle member 120 and configured to latch and lock the inner sleeve 140 in at least one position relative to the handle member 120, as will be discussed in more detail in relation to FIGS. 4A-4B.

The assembly 170 may include a release button 190 coupled to the locking element 171. The release button 190 may be configured to unlock the locking element 171, as will be described in more detail in relation to FIGS. 4A-4B. As shown in FIG. 1B, when the locking element 171 locks the inner sleeve 140, the proximal end 144 of the inner sleeve 140, the proximal end (e.g., driver bit 118) of the driver shank 110 and the proximal end 135 of the outer sleeve 130 may be aligned. This may cause the driver shank 110 to be mated with the socket of the bone fastener 250, the collet member 145 slipped over the head 252 of the bone fastener 250 and the proximal end of the outer sleeve 130 parallel and overlapping the collet member 145.

An unlocked position of the locking element 171 corresponds to an unlocked state of the inner sleeve 140. This may allow a portion of the length of the inner sleeve to extend past the first (bottom) end of the handle member 120 such that the proximal end 144 of the inner sleeve 140 and the proximal end of the driver shank 110 extend past the proximal end 135 of the outer sleeve 130. The surgeon or a device may visually inspect the location of the driver bit 118 relative to the head of the bone fastener 250.

The locking element 171 may include a plate 162 and a reciprocating lever arm 174. The reciprocating lever arm 174 may include an elbow 176 that oscillates, about the plate 162, in a first direction or a second direction. The plate 162 may be spring biased so that the transitioning of the locking element 171 between a locked position and an unlocked position may be smooth.

The locking element 171 may include a lever 178 accessible externally from the handle member 120. The elbow 176 may be configured to oscillate in a first direction along a surface of the plate 162 in response to an application of a force to the lever 178. The locking element 171 may include a follower arm 180 having a first end 182 pivotally coupled to the lever 178 and a second end 184 coupled to the inner sleeve's distal end 147. In operation, pressing the lever 178 of the locking element 171 may pivot the elbow 176 on the plate 162 and rotate the follower arm 180 in a first direction, which in turn may cause the inner sleeve 140 to retract into the handle member 120, as will be described in more detail in relation to FIG. 4A. The assembly 170 may include a support structure 160 and a spring 164 helically wrapped around the support structure 160. A top end of the support structure 160 may include the plate 152 under which is the spring 164.

The release button 190 may be coupled to the follower arm 180. In operation, application of a force to the release button 190 unlocks the follower arm 180 and reciprocating lever arm 174, as will be described in more detail in relation to FIG. 4B. This may cause the locking element 171 to unlock. Accordingly, the inner sleeve 140 is unlocked so that a portion of the length of the inner sleeve 140 and the driver shank 110 can extend a distance below the first (bottom) end of the handle member 120, as will be described in relation to FIG. 5C.

Figure 3:
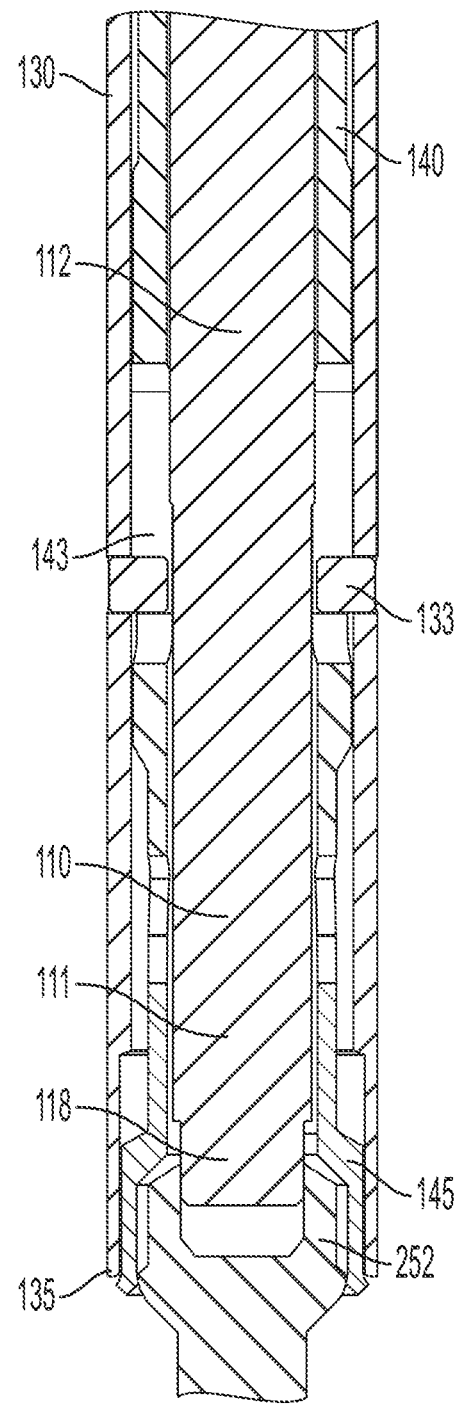
FIG. 3 is a cross-sectional view of a portion of the driver shank, outer sleeve, inner sleeve and the head of the bone fastener of FIG. 1B.

FIG. 3 is a cross-sectional view of a portion of driver shank 110, the outer sleeve 130, inner sleeve 140 and the head 252 of the bone fastener 250 of FIG. 1B. The driver shank 110 may include a first shank section 111 and a second shank section 112. The first shank section 111 has a first diameter. The second shank section 112 has a second diameter. The inner sleeve 140 may include a shoulder 143 formed on an interior surface of the inner sleeve 140. The shoulder 143 may limit the downward travel of the driver shank 110 within the inner sleeve 140. Specifically, the position of the shoulder 143 relative to the proximal end of the second shank section 112, aligns the ends of the inner sleeve 140 and the driver bit 118. As can be seen in FIG. 3, in some embodiments, the proximal end 135 of the outer sleeve may extend slightly past the shoulder 264 of the bone fastener 250.

The outer sleeve 130 may include a pin 133 to limit the travel of the inner sleeve 140 relative to the outer sleeve 130.

FIG. 4A illustrates a cross-sectional view of the locking element 171 in an unlocked position, the inner sleeve 140 in an extended position and the release button 190 in a recessed position. FIG. 4B illustrates a cross-sectional view of the locking element 171 in a locked position, the inner sleeve 140 in an extended position and the release button 190 in an extended position. The operation of FIGS. 4A-4B may also be described in relation to FIGS. 5A-5C that illustrate examples of an initial position, an engaged position and a locked position of the driver shank 110 relative to the bone fastener 250. The release button 190 is directly or indirectly coupled to the follower arm 180. Thus, when the follower arm 180 is pushed to lock the inner sleeve 140, the release button 190 is pushed by the follower arm 180 to the extended position, as in FIG. 4B. On the other hand, when the release button 190 is in the extended position, as in FIG. 4B, the user may press the release button 190 in the direction of ARROW 2 to unlock the locking element 171 by applying the force at a location in proximity to the first end 182 of the follower arm 180, thereby unlocking the locking element 171 and the inner sleeve 140.

Figure 5A:
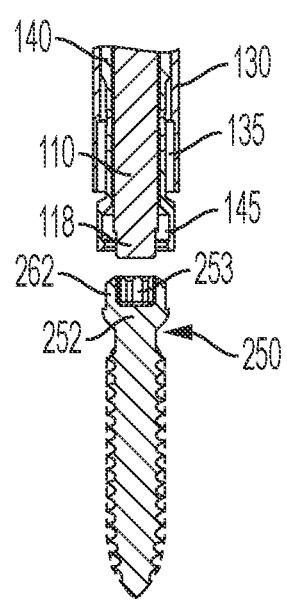
FIGS. 5A-5C illustrate examples of an initial position, an engaged position and a locked position of the driver shaft relative to the bone fastener.

In operation, the surgeon may start with the driver instrument 105 in an unlocked position and the inner sleeve 140 extended, as shown in FIG. 4A. The surgeon may then align the driver shank 110 or driver bit 118 with the bone fastener 250, as shown in FIG. 5A. In this position, the driver bit 118 may slightly extend past the proximal end 144 of the inner sleeve 140. The outer sleeve 130 may be positioned above the collet member 145 of the inner sleeve 140. Hence, both the driver bit 118 and the collet member 145 are exposed and out of the outer sleeve 130.

Figure 5B:
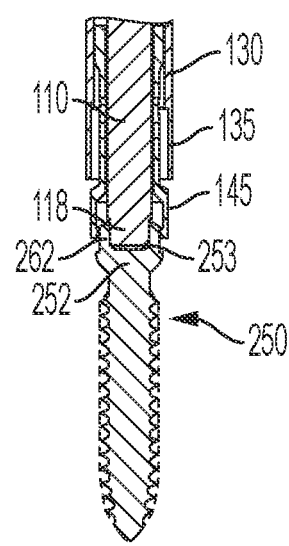

The surgeon may then press down on the driver shank 110 so that the driver bit 118 is received in the socket 253. The inner sleeve 140 includes a shoulder 143 which limits the extent the driver shank 110 may extend past the proximal end 144 of the inner sleeve 140. This may cause the inner sleeve 140 to also extend in the direction of the head of the bone fastener 250 such that a portion of the collet member 145 is slipped over a portion of the second head portion 262. In FIG. 5B, the collet member 145 may not be fully seated on the head 252.

In FIG. 4A, the release button 190 may be recessed within the handle member body 122. Pressing in the direction of ARROW 1 onto the lever 178 causes the locking element 171 to latch and lock and retract the inner sleeve 140, as shown in FIG. 4B. The locking element 171 may include a slide channel 405 formed in the handle member body 122. The upper end of the slide channel 405 corresponds to the locked position of the upper sleeve 140.

The locking element 171 may include a plate 410 coupled to the second end 184 of the follower arm 180 via pin 481. The inner sleeve 140 may be coupled to the plate 410 by a rail 415, for example. The plate 410 is shown in dashed lines to indicate its movement. The rail 415 may be coupled to the distal end 147 of the inner sleeve. The pin 481 slides in the slide channel 405 and rotates the second end 184 as the follower arm 180 moves under the force applied to the lever 178. As the follower arm 180 slides in the slide channel 405, the plate 410 may move the rail 415 coupled to the inner sleeve 140 to a locked position, as shown in FIG. 4B. As shown in FIGS. 4A and 4B, moving the lever 178: i) to the first lever position causes the rail 415 to travel in a first travel direction in the handle member 120 and retract the inner sleeve, from an extended position, into the handle member 120 (FIG. 4B); and ii) to the second lever position causes the rail 415 to travel in a second travel direction in the handle member 120 and extend a portion of the length of the inner sleeve 140, in a retracted position, out from the handle member (FIG. 4A). The positions of the lever 178 are not meant to be limiting as the first lever position may be the second lever position in some instances.

Figure 5C:
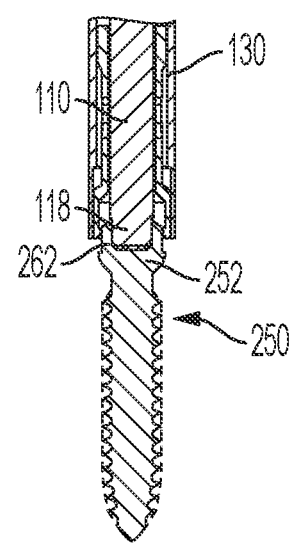

The lever 178 may include a tongue 479 to which the first end 182 of the follower arm 180 may be pivotally attached. As an application of force is applied to the lever 178, in the direction of ARROW 1, the elbow 176 at one end of the lever 178 rotates about the plate 162 so that the lever 178 rotates in the direction of the handle member body 122. As the lever 178 rotates in the direction of the handle member body 122, the follow arm 180 slides in the slide channel 405. After squeezing the lever 178 until the locking element 171 and the inner sleeve 140 are locked, the release button 190 may have a portion that is extended outside of the handle member body 122, as best seen in FIG. 4B. This action causes the both the inner sleeve 140 and the driver shank 110 to be retracted and locked. Furthermore, the outer sleeve 130 may be parallel and overlap the collet member 145, the driver bit 118 and the head 252, as shown in FIG. 5C. The driver bit 118 may be configured to engage the surfaces of socket 253 to rotate bone fastener 250 relative to and about a longitudinal axis. In some embodiments, socket 253 may have a cruciform, phillips, square, hexagonal, polygonal, star or hexalobe cross sectional configuration for disposal of a correspondingly shaped portion of the driver bit 118.

Pressing in the direction of ARROW 2 onto the release button 190 may cause the locking element 171 to unlock, which in turn may unlock the inner sleeve 140 so that the inner sleeve 140 may be extended. The orientation of the inner sleeve 140, the driver bit 118 and the outer sleeve 130 returns to the arrangement shown in FIG. 5B.

Figure 6A:
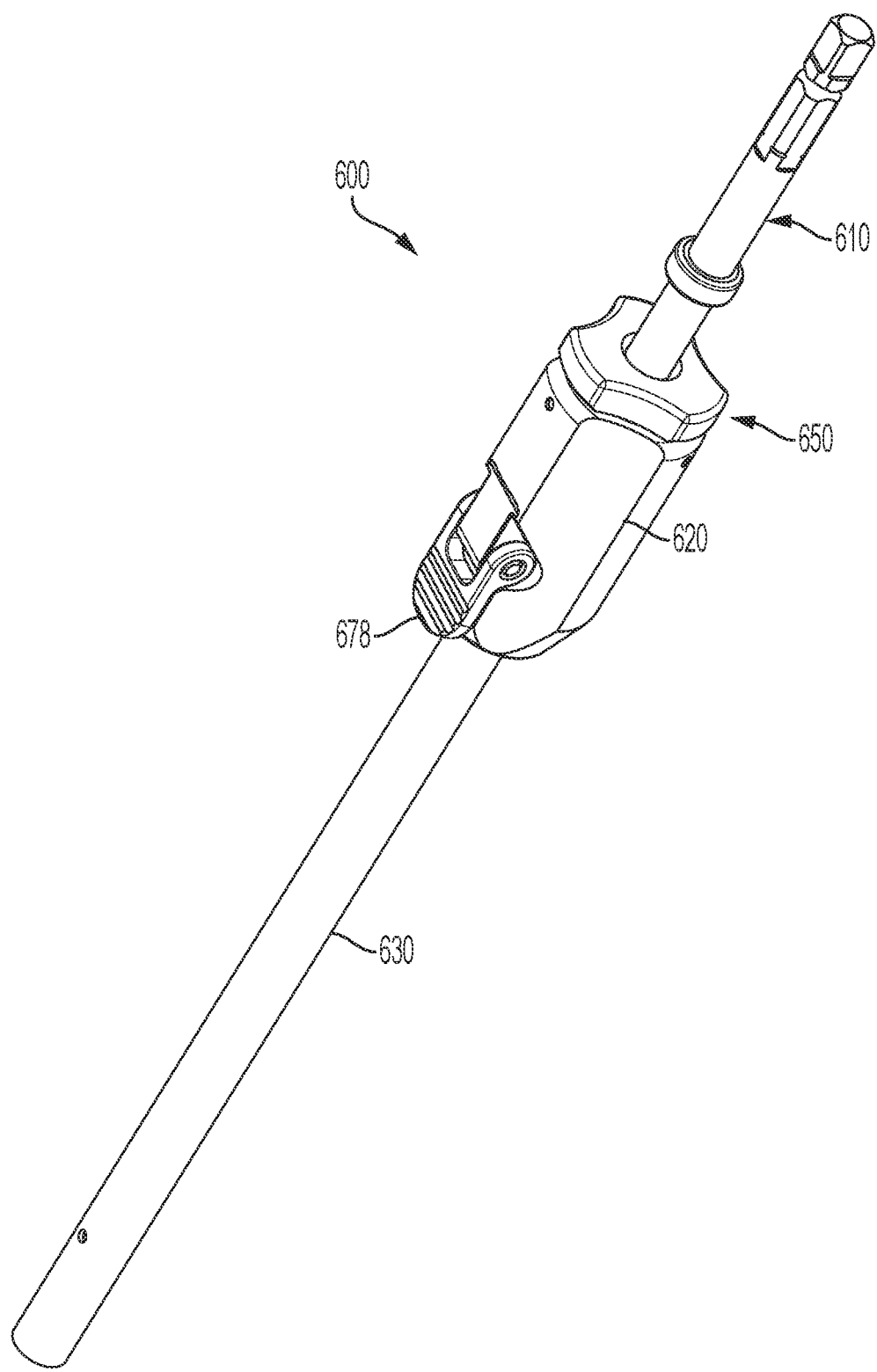
FIG. 6A is a perspective view that illustrates components of a surgical instrument system having a second driver instrument.
Figure 6B:
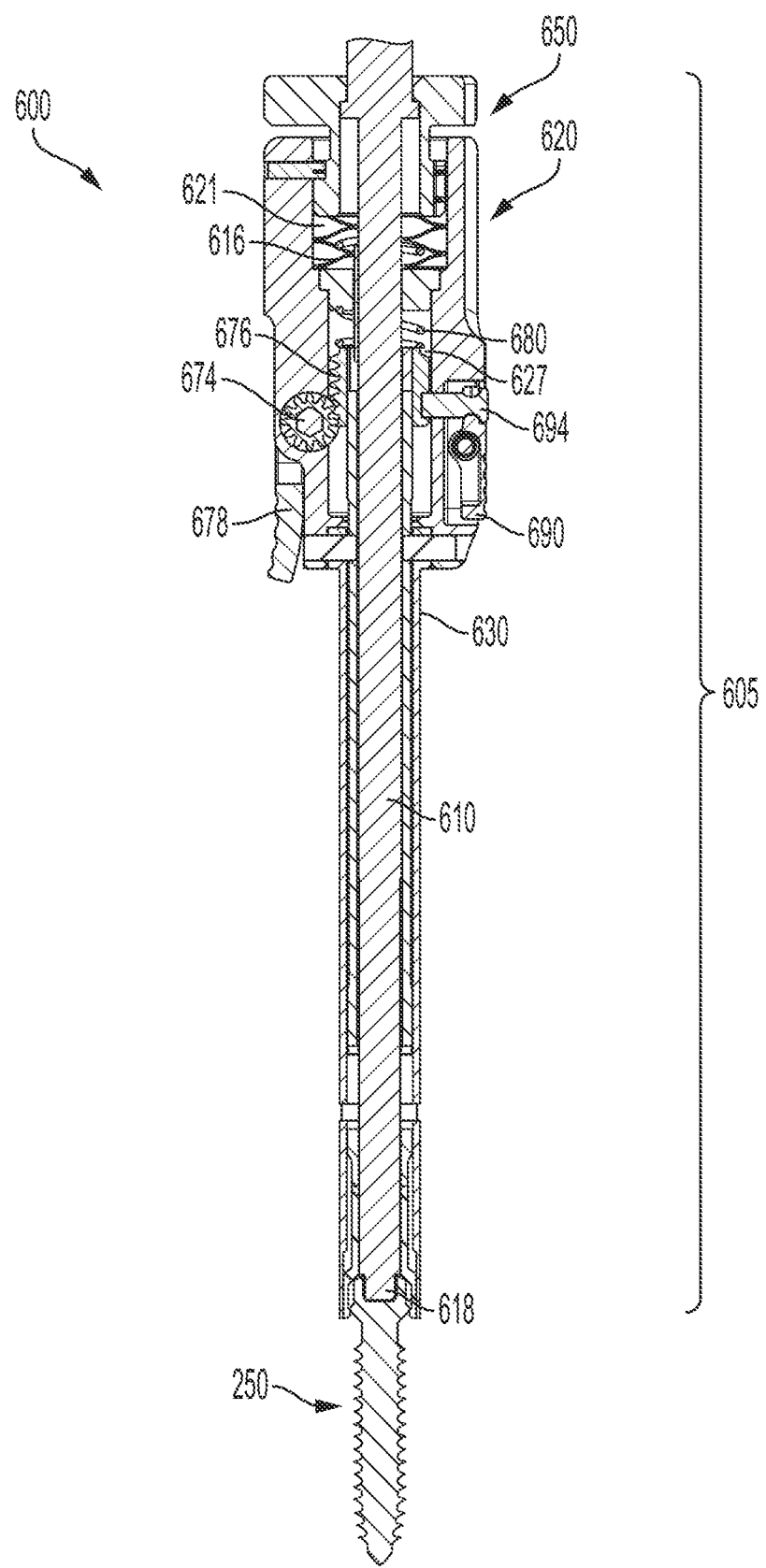
FIG. 6B is a cross-sectional view that illustrates components of a surgical instrument system having the second driver instrument.
Figure 7A:
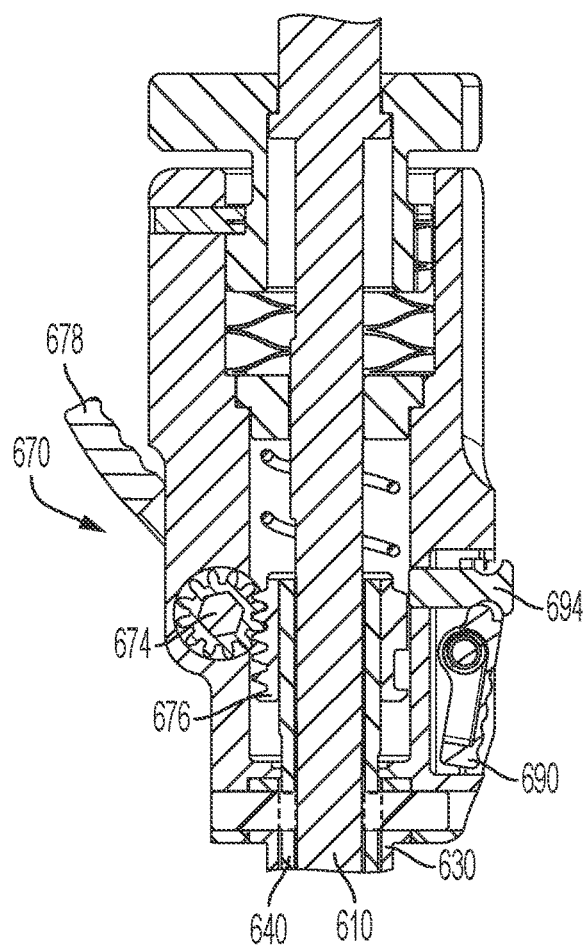
FIG. 7A illustrates a cross-sectional view of the second driver instrument of FIG. 6B when the inner sleeve is extended.
Figure 7B:
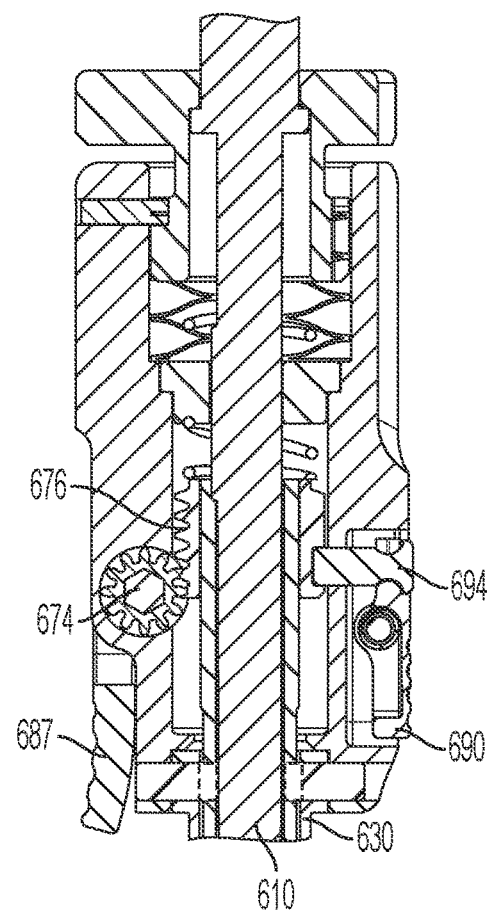
FIG. 7B illustrates a cross-sectional view of the second driver instrument of FIG. 6B when the inner sleeve is retracted.

FIGS. 6A-6B are perspective and cross-sectional views that illustrate components of a surgical instrument system 600 having a second driver instrument 605. The operation of the second driver instrument 605 will be described in relation to FIGS. 7A-7B. FIG. 7A illustrates a cross-sectional view of the second driver instrument of FIG. 6B when the inner sleeve is extended. FIG. 7B illustrates a cross-sectional view of the second driver instrument 605 of FIG. 6B when the inner sleeve 640 is retracted.

The second driver instrument 605 may include a sleeve actuator assembly 670, a handle member 620, an outer sleeve 630 and an inner sleeve 640. The outer sleeve 630 and inner sleeve 640 may be similar to the outer sleeve 130 and inner sleeve 140 described above in relation to FIG. 1B. The driver shank 110 and 610 are similar. For example, the driver shank 610 is mounted to the handle member 620 via mount 650. Hence, no further discussion will be provided about the mounting of the driver shank 610 to the handle member 620.

The handle member 620 includes a first cavity 621 and a second cavity 627. A spring 616 may be housed in the first cavity 621. The sleeve actuator assembly 670 being mounted and assembled in the second cavity 627. A spring 680 may be positioned in the second cavity 627 between the inner sleeve 640 and the first cavity 621.

The sleeve actuator assembly 670 that may cause the movement of the inner sleeve 640 to move between retracted and extended positions. The assembly 670 may include a sprocket wheel 674 having cogs and a track 676 configured to mate with the cogs of the sprocket wheel 674. The assembly 670 may include an actuating lever 678 coupled to the sprocket wheel 674. The track 676 may be affixed to the sleeve distal end within the handle member 620. The lever 678 coupled to the sprocket wheel may be moved from a first lever position to a second lever position, as shown in FIGS. 7A-7B. For example, moving the lever 678: i) to the first position causes the sprocket wheel 674 to rotate in a first direction of rotation and the track 676 to travel in a first travel direction in the handle member 620 and retract a portion of the length of the inner sleeve 640 into the handle member 620 (FIG. 7B); and ii) to the second position causes the sprocket wheel 674 to rotate in a second direction of travel and the track 676 to travel in a second travel direction in the handle member 620 and extend a portion of the length of the inner sleeve 640 out from the handle member 620 (FIG. 7A). The spring 680 may assist in returning the lever 678 as shown in FIG. 7A to the position shown in FIG. 7B.

The sleeve actuator assembly 670 may include a release latch 694 coupled to the handle member 620 and releasably coupled to the track 676, the release latch 694 may include a locked position, as shown in FIG. 7B, to lock the track 676 and an unlocked position, as shown in FIG. 7A, to unlock the track 676. The locked state of the track 676 also locks the inner sleeve 640. The unlocked state of the track 676 also unlocks the inner sleeve 640. The track 676 may include a locking notch 687 into which one end of the release latch 694 may be become recesses. The release arm 690 may be coupled to a release latch 694. Pressing the release latch 694, as shown in FIG. 7A extends the release latch 694 out of the locking notch 687 so that the track is unlocked. When, the track 676 travels in the direction of the release latch 694, one end of the track 676 will automatically engage with the locking notch 687.

The orientation of the outer sleeve 630, the inner sleeve 640 and the driver bit 618 relative to bone fastener 250 will be essentially the same as shown in and described in relation to FIGS. 5A-5C, in relation to retracted and extended positions of the inner sleeve 640.

Figure 8A:
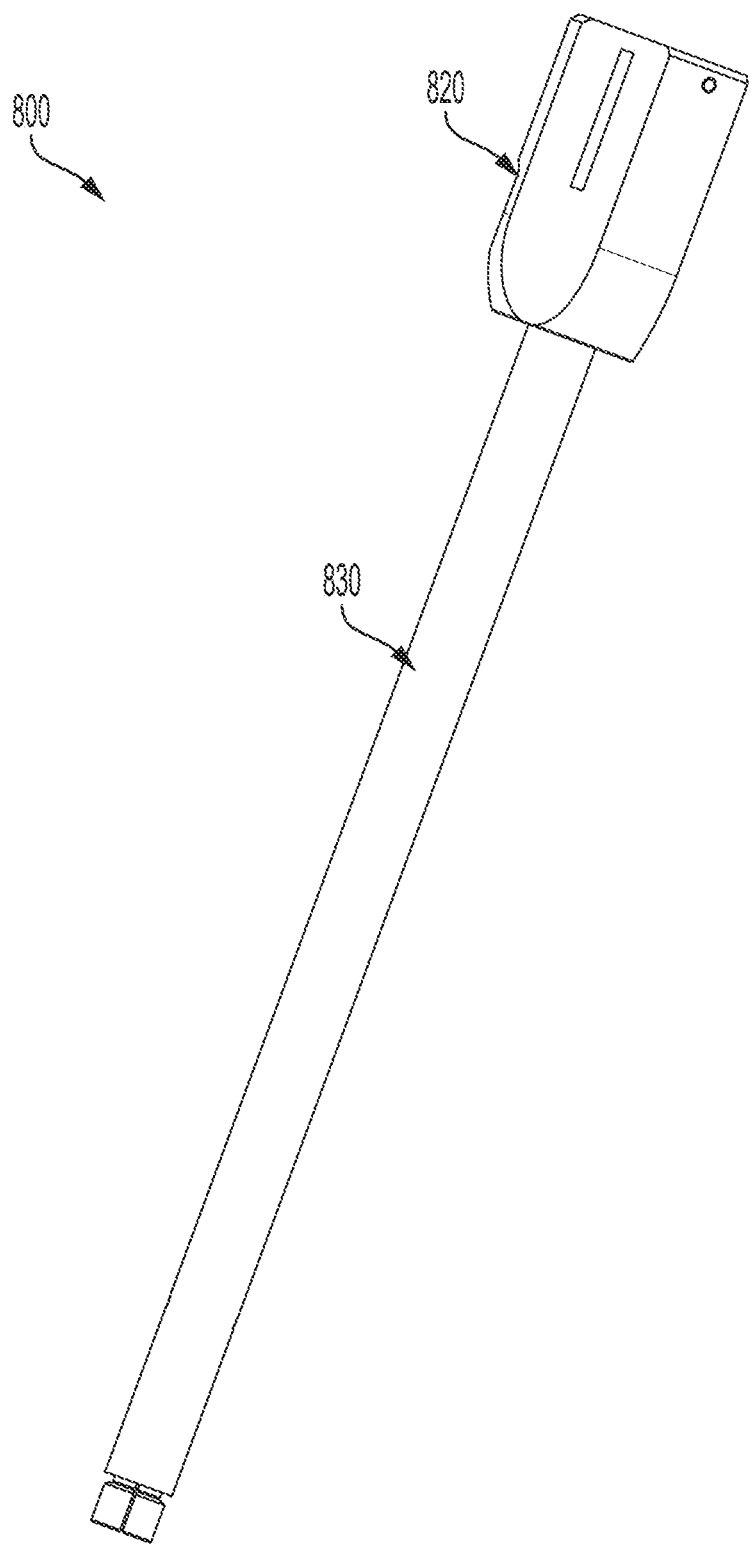
FIG. 8A is a perspective view that illustrates components of a surgical instrument system having a third driver instrument
Figure 8B:
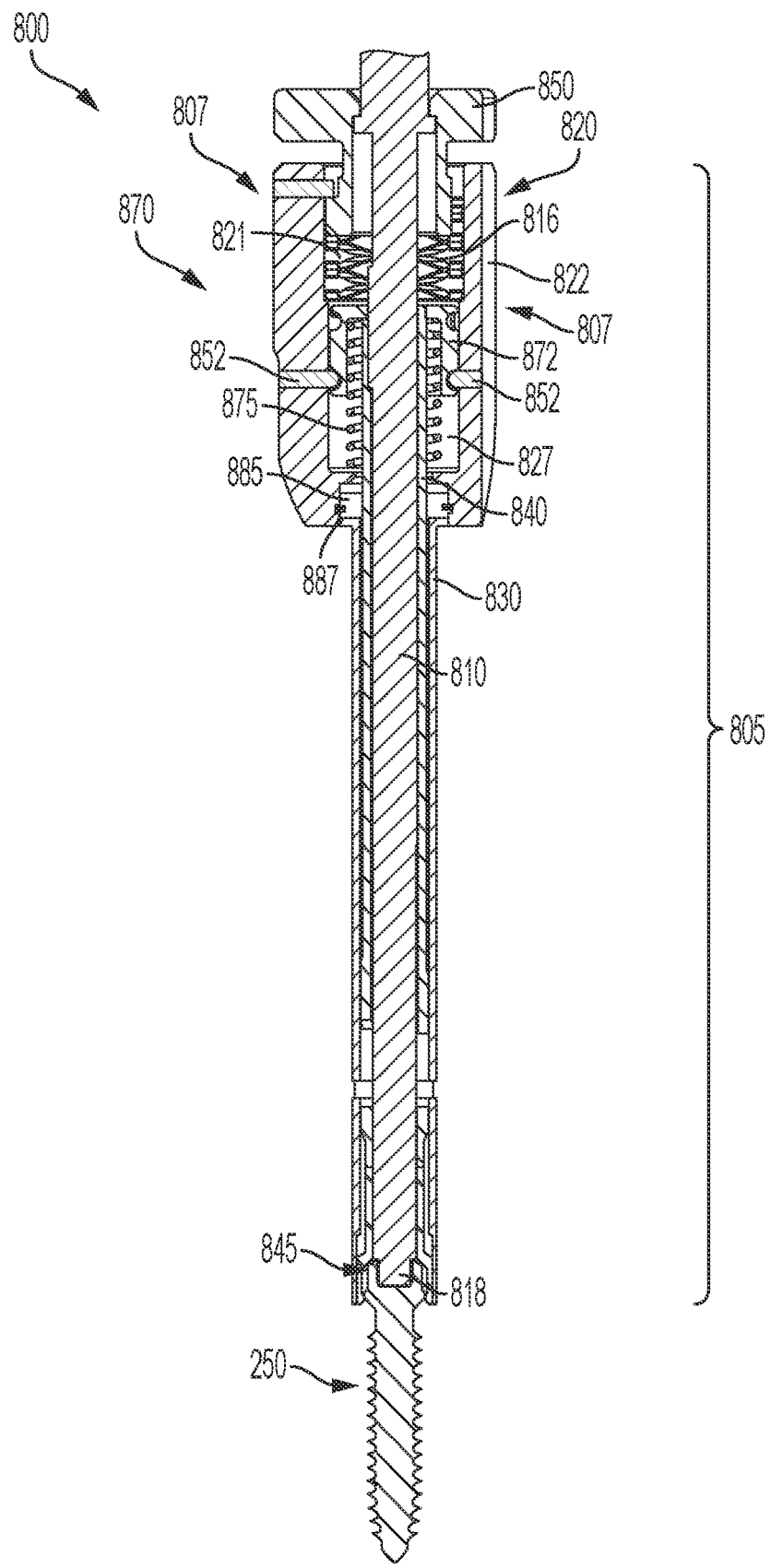
FIG. 8B is a cross-sectional view that illustrates components of a surgical instrument system having the third driver instrument.
Figure 10A:
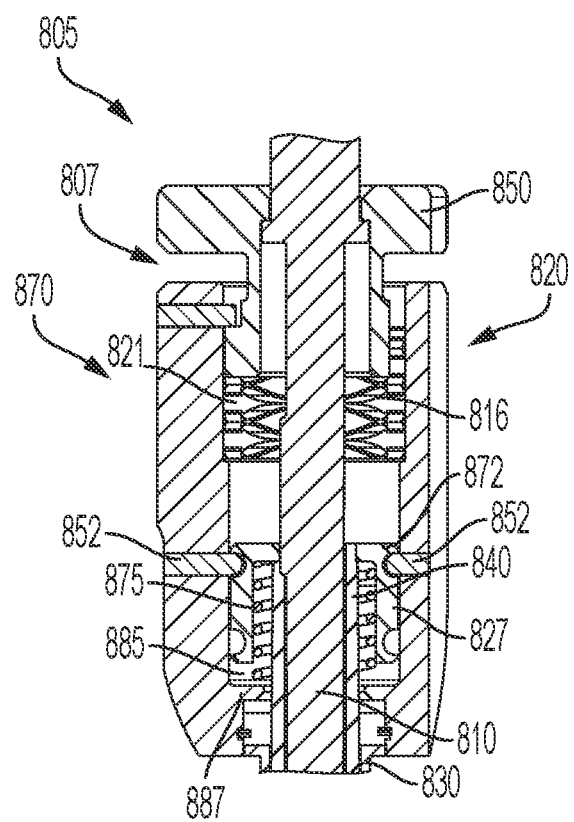
FIG. 10A illustrates a cross-sectional view of the third driver instrument of FIG. 8B when the inner sleeve is extended.
Figure 10B:
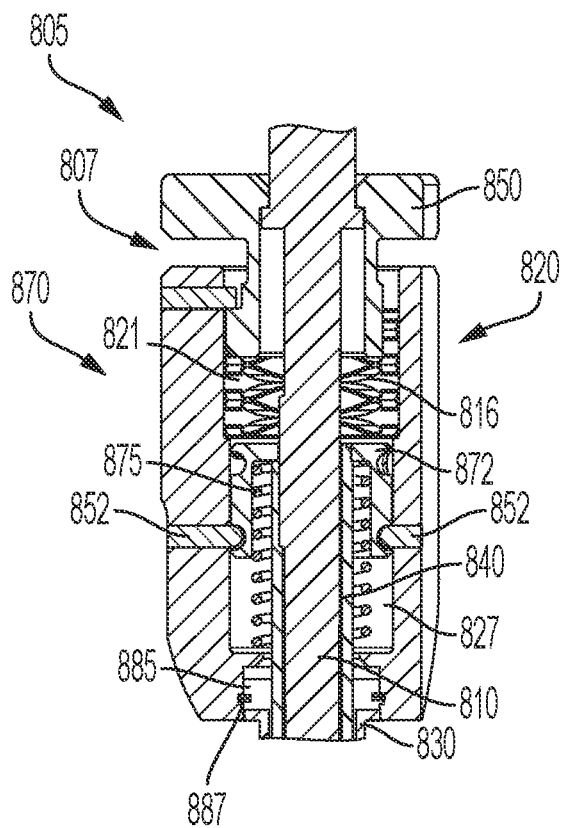
FIG. 10B illustrates a cross-sectional view of the third driver instrument of FIG. 8B when the inner sleeve is retracted.

FIGS. 8A-8B are perspective and cross-sectional views that illustrate components of a surgical instrument system 800 having a third driver instrument 805. The operation of the driver instrument 805 will be described in relation to FIGS. 10A-10B. FIG. 10A illustrates a cross-sectional view of the third driver instrument 805 of FIG. 8B when the inner sleeve 840 is extended from the first (bottom) end of the handle member 820. FIG. 10B illustrates a cross-sectional view of the third driver instrument 805 of FIG. 8B when the inner sleeve 840 is retracted into the handle member 820.

The driver instrument 805 may include a sleeve actuator assembly 870, a handle member 820, an outer sleeve 830 and an inner sleeve 840. The outer sleeve 830 and inner sleeve 840 may be essentially the same as the inner and outer sleeves 130 and 140 described above in relation to FIG. 1B. The driver shank 110 and 810 are similar Hence, the discussion above regarding driver shank 110 may be applied in whole or in part to driver shank 810, including with regard to mounting to the handle member. No further discussion will be provided about the mounting of the driver shaft 810 to the handle member 820.

The assembly 870 may include a helical cam member 872 concentric with and affixed to the distal end of the inner sleeve 840. The helical cam member 872 will be describes in more detail in relation to FIGS. 9A-9B. The handle member 820 may include a first cavity 821 and a second cavity 827. The first cavity 821 may be configured to mount therein the driver shank 110 via mount 850. The shank adapter 807 may include a spring 816 housed in the first cavity 821. The second cavity 827 is configured to house therein the helical cam member 872 and spring 875 within the helical cam member 872.

The handle member 820 may be rotational. The assembly 870 may include a disc 885. The handle member 820 may include a rib 887 configured to engage the disc 885 so that the handle member 820 may rotate at least a portion around the disc 885 to retract or extend the inner sleeve 840. The handle member 820 may rotate relate to the outer sleeve 830 and the inner sleeve 840.

Figure 9A:
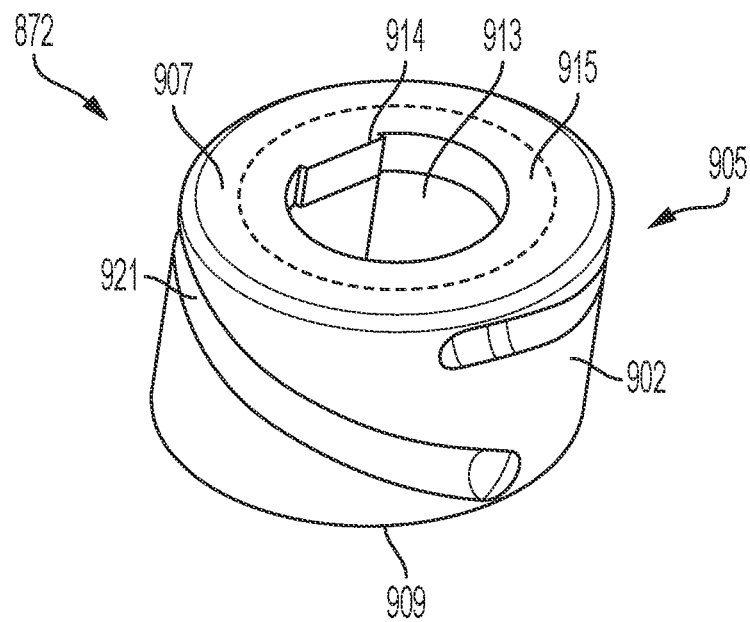
FIGS. 9A-9B are top and bottom perspective views of the helical cam member.
Figure 9B:
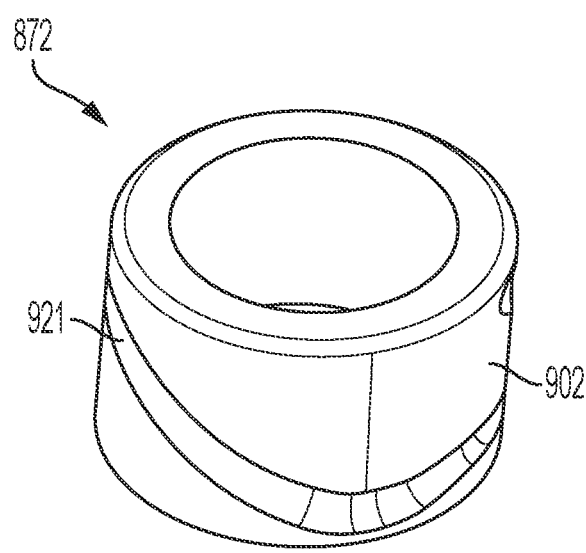

FIGS. 9A-9B are top and bottom perspective views of the helical cam member 872. The helical cam member 872 may include a hollow cylindrical member 905 having a top end 907, a bottom end 909 and a wall 902. The wall 902 extends between the top end 907 and the bottom end 909. The wall 902 is an annulus. The helical cam member 872 may include a helical cam groove 921 circumferentially formed in the wall 902. The diameter of the annulus may be reduced at the top end 907. For example, the top end 907 may include a flange 915 configured to reduce the diameter of the annulus. The diameter of the opening in the flange 915 may be dimensioned to receive therethrough the body of the inner sleeve 840, such that the body slides through the opening. The annulus may include a flat surface section 914 to align the inner sleeve in position relative to the annulus.

Returning again to FIG. 8B, the spring 875 which may be housed within the annulus between the inner sleeve and the interior side of wall 902. The flange 915 may compress of the spring 875, as shown in FIG. 10A.

The assembly 870 may include at least one pin 852 coupled to the handle member body 822. The at least one pin 852 is oriented to engage the helical cam groove 921. By way of non-limiting example, the handle member body 822 is rotationally coupled to the inner sleeve 840 such that rotation of the handle member body 822 causes the helical cam member 872 to rotate as the at least one pin 852 remains engaged with a portion of the groove 921. When turning of the helical cam member 872 by way of rotation of the handle member 820, in a first direction, the inner sleeve 840 may be caused to follow to a retracted position into the handle member 820, as shown in FIG. 10B. This arrangement locks the position of the inner sleeve 940 in the retracted position. In operation, turning of the handle member 820: i) in a first direction causes the helical cam member 872 to travel in a first travel direction in the handle member 820 to cause the inner sleeve 840, in an extended position, to retract into the handle member 820 (FIG. 10B); and ii) in a second direction causes the helical cam member 872 to travel in a second travel direction in the handle member 820 to cause the inner sleeve 840, in a retracted position, to extend the portion of the length of the inner sleeve 840 out from the handle member 820.

In some embodiments, the rotation of the handle member may be from 0-180°, for example. Additionally, the first direction of the helical cam member and the second direction of the helical cam member are not meant to be limiting.

The orientation of the outer sleeve 830, the inner sleeve 840 and the driver bit 818 relative to bone fastener 250 will be essentially the same as shown in and described in relation to FIGS. 5A-5C, in relation to retracted and extended positions of the inner sleeve 840.

In some embodiments, surgical system 100, 600 or 800 may include one or a plurality of plates, connectors and/or bone fasteners for use with a single vertebral level or a plurality of vertebral levels. In some embodiments, one or more of bone fasteners may be engaged with tissue in various orientations, such as, for example, series, parallel, offset, staggered and/or alternate vertebral levels. In some embodiments, one or more bone fasteners may comprise multi-axial screws, sagittal angulation screws, pedicle screws, mono-axial screws, uni-planar screws, facet screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A driver instrument, comprising:
   a driver shank having a proximal end including a head connector for a bone construct;
   an inner sleeve having a length and configured to receive the driver shank therein, the inner sleeve and the driver shank have a non-threaded connection;
   a handle member having a first end and a second end;
   an outer sleeve connected to the second end of the handle member and being concentric with the inner sleeve; and
   a sleeve actuator assembly coupled to the handle member and engaged with the inner sleeve via a non-threaded mechanical connector preventing rotation of the inner sleeve relative to the handle member, the non-threaded mechanical connector enabling selective transitioning of the inner sleeve between an unlocked position in which the inner sleeve is able to be slid in two opposing directions aligned with a longitudinal axis of the handle member and a locked position in which sliding of the inner sleeve relative to the handle member is prevented
   wherein the non-threaded mechanical connector comprises a reciprocating lever arm, a follower arm pivotally coupled to the reciprocating arm, and a release button coupled to the follower arm;
   wherein the release button extends from the handle member when the inner sleeve is retracted into the handle member; and
   wherein application of a force to the release button unlocks the follower arm and reciprocating arm to release the inner sleeve such that the inner sleeve is extendable out from the handle member.

2. The driver instrument of claim 1, wherein the inner sleeve includes:
   a sleeve distal end;
   a sleeve proximal end;
   an elongated hollow cylindrical body between the sleeve distal end and the sleeve proximal end; and
   a shoulder formed on an interior surface of the elongated hollow cylindrical body, the shoulder is configured to orient the proximal end of the driver shank relative to the sleeve proximal end.

3. The driver instrument of claim 2, wherein the sleeve actuator assembly further comprises:
   a lever having a first lever position and a second lever position;
   the follower arm having a first end pivotally coupled to the reciprocating lever arm and a second end coupled to the sleeve distal end; and
   a rail coupled to the follower arm and the sleeve distal end,
   wherein moving the lever:
   i) to the first lever position causes the rail to travel in a first travel direction in the handle member and retract the inner sleeve, from an extended position, into the handle member, and
   ii) to the second lever position causes the rail to travel in a second travel direction in the handle member and extend the inner sleeve, in a retracted position, from the handle member.

4. A method, comprising:
   providing the driver instrument of claim 1; and
   engaging the driver shank with a bone construct when the inner sleeve is an extended position; and
   rotating the bone construct with the driver shank when the inner sleeve is a retracted position.

5. The method of claim 4, further comprising selectively moving the sleeve actuator assembly coupled to the inner sleeve:
   i) to a first position to retract the inner sleeve into a handle member; or ii) to a second position to extend the inner sleeve from the handle member.

6. A system, comprising:
a bone construct having a head; and
a surgical driver instrument including:
a driver shank having a proximal end including a head connector for axial rotation of the bone construct;
an inner sleeve having a length and configured to receive the driver shank therein, the inner sleeve and the driver shank have a non-threaded connection;
a handle member having a first end and a second end;
an outer sleeve connected to the second end of the handle member and being concentric with the inner sleeve; and
a sleeve actuator assembly coupled to the handle member and engaged with the inner sleeve via a non-threaded mechanical connector preventing rotation of the inner sleeve relative to the handle member, the non-threaded mechanical connector enabling selective transitioning of the inner sleeve between an unlocked position in which the inner sleeve is able to be slid in two opposing directions aligned with a longitudinal axis of the handle member and a locked position in which sliding of the inner sleeve relative to the handle member is prevented;
wherein the non-threaded mechanical connector comprises a reciprocating lever arm, a follower arm pivotally coupled to the reciprocating arm, and a release button coupled to the follower arm;
wherein the release button extends from the handle member when the inner sleeve is retracted into the handle member; and
wherein application of a force to the release button unlocks the follower arm and reciprocating arm to release the inner sleeve such that the inner sleeve is extendable out from the handle member.

7. The system of claim 6, wherein the inner sleeve includes:
a sleeve distal end;
a sleeve proximal end;
an elongated hollow cylindrical body between the sleeve distal end and the sleeve proximal end; and
a shoulder formed on an interior surface of the elongated hollow cylindrical body, the shoulder is configured to orient the proximal end of the driver shank relative to the sleeve proximal end.

8. The system of claim 7, wherein the sleeve actuator assembly further comprises:
a lever having a first lever position and a second lever position;
the follower arm having a first end pivotally coupled to the lever arm and a second end coupled to the sleeve distal end; and
a rail coupled to the follower arm and the sleeve distal end,
wherein moving the lever:
i) to the first lever position causes the rail to travel in a first travel direction in the handle member and retract the inner sleeve, from an extended position, into the handle member, and
ii) to the second lever position causes the rail to travel in a second travel direction in the handle member and extend the inner sleeve, in a retracted position, from the handle member.

9. The system of claim 7, wherein the sleeve proximal end comprises a collet member.

10. The system of claim 9, wherein the head of the bone construct includes:
a socket;
a first head portion;
a second head portion having the socket formed therein; and
a shoulder demarcating the first head portion and the second head portion,
wherein when the inner sleeve is retracted in the handle member, the outer sleeve is parallel and overlaps the collet member.

\* \* \* \* \*